Figure 1:
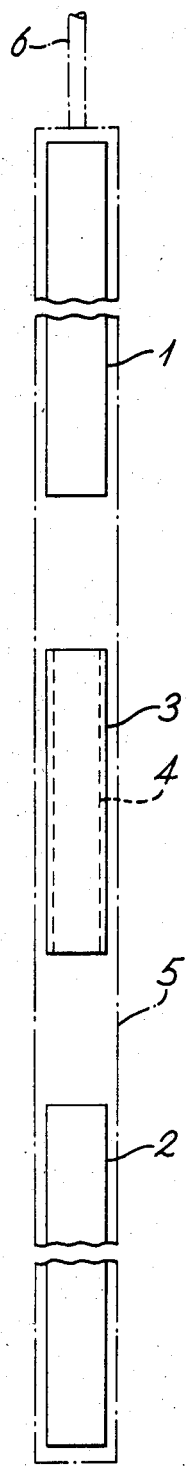

United States Patent [19]

Clow et al.

[11] Patent Number: 4,629,986
[45] Date of Patent: Dec. 16, 1986

[54] NUCLEAR MAGNETIC LOGGINS

[75] Inventors: Hugh Clow, Maidenhead; William S. Percival; Peter E. Walters, both of London, all of England

[73] Assignee: National Research Development Corp., London, England

[21] Appl. No.: 613,402

[22] Filed: May 24, 1984

[30] Foreign Application Priority Data

Jun. 9, 1983 [GB] United Kingdom ................. 8315866

[51] Int. Cl.$^4$ ............................................ G01R 33/20
[52] U.S. Cl. ..................................... 324/303; 324/318
[58] Field of Search ............... 324/300, 303, 318, 319, 324/322, 346, 220, 221

[56] References Cited

U.S. PATENT DOCUMENTS

| | | | |
|---|---|---|---|
| 2,968,761 | 1/1961 | Zimmerman | 324/303 |
| 3,597,681 | 8/1971 | Huckabay | 324/303 |
| 3,617,867 | 11/1971 | Herzog | 324/303 |
| 4,350,955 | 9/1982 | Jackson et al. | 324/303 |
| 4,528,508 | 7/1985 | Vail, III | 324/303 |

Primary Examiner—Michael J. Tokar
Attorney, Agent, or Firm—Cushman, Darby & Cushman

[57] ABSTRACT

An elongated probe suitable for lowering down a borehole for nuclear magnetic logging has a pair of similar cylindrical magnets 1 and 2 separated by a gap in which a solenoid 3 is symmetrically disposed. The solenoid has a core 4 of high permeability ferrimagnetic material and has a length preferably equal to half the length of the gap. The magnets 1 and 2 and solenoid 3 with its core 4 are contained within a hollow cylindrical casing 5 of non-magnetic material.

5 Claims, 5 Drawing Figures

NUCLEAR MAGNETIC LOGGINS

Nuclear magnetic logging is a borehole logging technique in which information relating to a fluid (such as water or oil) in a geological formation is derived by performing nuclear magnetic resonance (NMR) experiments with a probe located in a borehole extending through the formation. The relevant nuclei are normally protons, and the measured parameters in respect of the fluid may include spin density and the relaxation times commonly denoted $T_1$ and $T_2$. Hitherto it has been the usual practice in nuclear magnetic logging to arrange for the polarising field $H_1$ which excites the NMR to be a steady field generated by a constant current flowing through a coil in the probe, and to utilise the earth's magnetic field as the field $H_0$ about which the nuclear spins precess during signal acquisition; this arrangement of course differs from the one used in conventional NMR spectrometers, in which the field $H_0$ is generated by a magnet system and the field $H_1$ is generated by a high frequency alternating current flowing through a coil.

Although offering the advantage over other borehole logging techniques of obtaining signals directly from an extractable fluid, nuclear magnetic logging has not so far been put to widespread use. A major problem encountered with the technique is that of ensuring that the desired NMR signals are not swamped by signals arising either from fluid in the borehole or from fluid in a disturbed region of rock immediately surrounding the borehole (which region will not usually be typical of the bulk of the formation). This selectivity problem is accentuated for the field arrangement normally used because with that arrangement the sensitivity falls off rapidly with distance from the axis of the borehole. Previous attempts to deal with this problem have involved the use of specially doped fluid in the borehole, but this is undesirable when logging water wells. It would in any event be preferable for the probe itself to be of a form inherently capable of affording a high degree of the desired spatial selectivity.

The present invention seeks to meet this requirement by providing a probe for use in nuclear magnetic logging, the probe being of elongated form suitable for lowering down a borehole with its longitudinal axis extending vertically, and incorporating a pair of similar cylindrical permanent magnets disposed with their axes substantially coincident with said longitudinal axis and separated by a gap extending between like poles of the two magnets, a solenoid disposed about the centre of in said gap coaxial with the magnets, and a core of magnetic material disposed within the solenoid.

Preferably the solenoid is disposed symmetrically in said gap. Preferably also the core of the solenoid is of a high permeability ferrimagnetic material.

In use of such a probe the field $H_1$ is generated by a high frequency current flowing through the solenoid, which may also suitably serve to pick up the NMR signals; it will normally be appropriate to utilise conventional pulsed NMR techniques. The field $H_0$ generated by the magnets and shaped by the core within the solenoid exhibits an inhomogenous form such that appropriate spatial selectivity can be achieved by frequency discrimination, suitably by filtering the received NMR signals prior to detection; the basis for this is of course the fundamental equation $F = \gamma H/2\pi$, relating resonance frequency F to magnetic field H ($\gamma$ being the gyromagnetic ratio for the relevant nuclei). The provision of the core within the solenoid is also significant in enabling a satisfactory signal to noise ratio to be achieved.

The invention will be further described and explained with reference to the accompanying drawings, in which:

FIG. 1 is a diagram illustrating the layout of the essential components of one probe in accordance with the invention; and FIGS. 2(a) to 2(d) are explanatory diagrams.

Referring to FIG. 1, the probe includes a pair of similar permanent magnets 1 and 2 fabricated from a material of the type incorporating a cobalt-samarium alloy with a polymeric binder. The magnets 1 and 2 are of cylindrical form of length about 50 cm and diameter about five cm, and are disposed coaxially with like poles facing each other and separated by a gap of length about 50 cm. Symmetrically disposed within this gap and coaxial with the magnets 1 and 2 is a solenoid 3 having a length of about 25 cm and an external diameter equal to the diameter of the magnets 1 and 2. The solenoid 3 consists of a copper winding formed on a core 4 of a high permeability ferrimagnetic material, for example constituted by a rod of manganese-zinc ferrite material. In a complete probe the components 1 to 4 are mounted coaxially within the cylindrical casing of nonmagnetic material, which is indicated in outline at 5 and which has an external diameter of about 7 cm; the casing 5 may also house at least part of the electronic circuitry (not shown) required to carry out the NMR experiments. The casing 5 is suspended at one end from one end of a cable (indicated in outline at 6) by means of which the probe can be lowered down a borehole with the longitudinal axis of the casing 5 extending vertically; the cable 6 incorporates conductors via which energising and/or signal currents can be passed between the probe and the part of the logging equipment located at the surface.

Figure 2A:
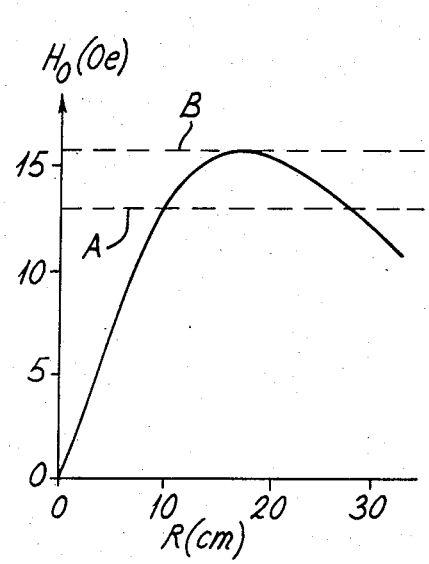

In explaining the design of the probe illustrated in FIG. 1, it is convenient to denote the longitudinal axis of the probe as the Z-axis and to define the plane $Z=0$ as that plane perpendicular to the Z-axis which bisects the gap between the magnets 1 and 2. In respect of the requirement for spatial selectivity it is assumed that it is desired to discriminate as far as possible against any NMR signals arising from points less than say 10 cm from the Z-axis. It is appropriate firstly to consider an arrangement similar to that shown in FIG. 1 but with the core 4 omitted; because of the symmetry of the arrangement about the plane $Z=0$, at any point in this plane the field $H_0$ generated by the magnets is directed wholly radially while the field $H_1$ generated by the solenoid is directed parallel to the Z-axis and hence perpendicular to the field $H_0$. FIG. 2(a) illustrates for this arrangement how the strength of the field $H_0$ varies with distance R from the Z-axis for points in the plane $Z=0$; the maximum value of the field occurs for a value of R equal to $G/2\sqrt{2}$, where G is the length of the gap between the magnets. So far as points in the plane $Z=0$ are concerned, the spatial selectivity requirement can be met by restricting the detected NMR signals to a band of resonance frequencies corresponding to values of the field $H_0$ lying between the lines A and B in FIG. 2(a); for protons this band will be approximately 56-67 kHz. It is however necessary to consider also points away from the plane $Z=0$, and in FIG. 2(b) the shaded area represents (for positive values of Z) the area in any plane passing through the Z-axis for which the proton resonance frequency will lie within the quoted frequency band; there is of course a similar area for negative values of Z and the volume of effective sensitivity can be obtained by rotation of these two areas about the Z-axis. As will be seen from FIG. 2(b), the spatial selectivity is far from ideal for the arrangement being considered, since some 20% of the detected NMR signals would arise from points within 10 cm of the Z-axis. Moreover, calculations indicate that for such an arrangement the signal to noise ratio would be impracticably low.

Figure 2C:
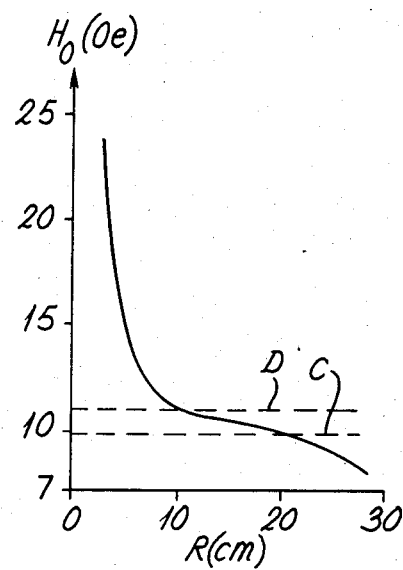
Figure 2B:
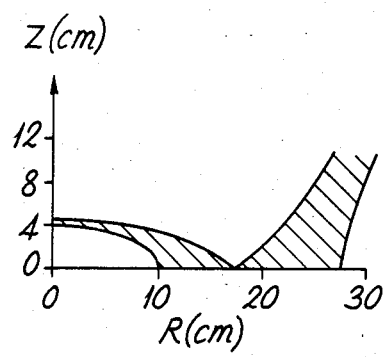
Figure 2D:
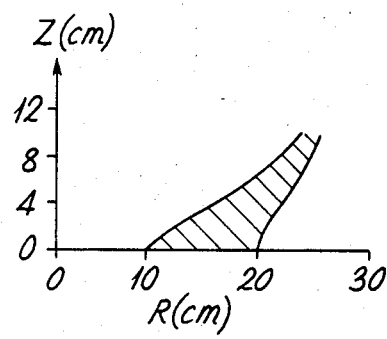

The effect of the inclusion of the core 4 can be appreciated from FIGS. 2(c) and 2(d), which are diagrams respectively similar to FIGS. 2(a) and 2(b) but relating to the probe illustrated in FIG. 1. In this case the lines C and D in FIG. 2(c) and the boundaries of the shaded area in FIG. 2(d) correspond respectively to proton resonance frequencies of 41.8 and 46.2 kHz; by filtering the received NMR signals with a filter having a pass band matching these values it should be possible to ensure that upwards of 95% of the detected signals emanate from points more than 10 cm from the Z-axis and hence properly representative of the formations under investigation. Moreover due to the effect of the high permeability core increasing the Q factor of the coil it is estimated that the signal to noise ratio should be several times higher for the probe illustrated in FIG. 1 than for the similar arrangement with the core 4 omitted. In particular the signal to noise ratio should be high enough to enable accurate measurements of proton spin density (and hence free fluid index) to be obtained with a signal averaging time of three or four seconds, which would for example enable a vertical resolution of about 25 cm to be achieved with a reasonable logging rate of about four metres/minute. The probe can of course also be used for making measurements of one or other of the relaxation times $T_1$ and $T_2$, but in this case it is envisaged that the probe would be maintained stationary with the vertical resolution being about 15 cm.

We claim:

1. A probe for use in nuclear magnetic logging, the probe being of elongated form suitable for lowering down a borehole with its longitudinal axis extending vertically, and incorporating a pair of similar cylindrical permanent magnets disposed with their axes substantially coincident with said longitudinal axis and separated by a gap extending between like poles of the two magnets, a solenoid disposed about the centre of said gap coaxial with the magnets, and a core of magnetic material disposed within the solenoid.

2. The probe as claimed in claim 1 in which the solenoid is disposed symmetrically in said gap.

3. The probe as claimed in claim 1 in which the length of the solenoid is approximately equal to half the length of the gap between the magnets.

4. The probe as claimed in claim 1 in which the core is of a high permeability ferrimagnetic material.

5. The probe as claimed in claim 1 in which the magnets are fabricated from material incorporating a cobalt/samarium alloy.

* * * * *